(12) United States Patent
Gunday et al.

(10) Patent No.: US 10,058,235 B2
(45) Date of Patent: Aug. 28, 2018

(54) STEERABLE CATHETER

(75) Inventors: Erhan H. Gunday, Great Neck, NY (US); Lawrence J. Gerrans, San Anselmo, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 2004 days.

(21) Appl. No.: 13/037,874

(22) Filed: Mar. 1, 2011

(65) Prior Publication Data

US 2012/0226103 A1    Sep. 6, 2012

(51) Int. Cl.
*A61B 1/005* (2006.01)
*A61M 25/092* (2006.01)
(Continued)

(52) U.S. Cl.
CPC ........ *A61B 1/0057* (2013.01); *A61B 1/00154* (2013.01); *A61B 1/015* (2013.01); *A61M 25/0155* (2013.01); *A61B 1/00039* (2013.01); *A61M 25/001* (2013.01); *A61M 25/005* (2013.01); *A61M 25/0012* (2013.01);
(Continued)

(58) Field of Classification Search
CPC .......... A61M 25/0105; A61M 25/0136; A61M 25/0138; A61M 25/0141; A61M 25/0144; A61M 25/0147; A61M 25/0152; A61M 25/0155; A61M 25/001; A61M 25/005; A61M 25/0012; A61M 25/0013; A61M 25/0023; A61M 25/0026; A61M 25/0052; A61M 25/0053; A61M 25/0054; A61M 2025/0025; A61M 2025/0024;
(Continued)

(56) References Cited

U.S. PATENT DOCUMENTS 3,773,034 A    11/1973    Burns et al.
4,685,473 A    8/1987    Karcher et al.
(Continued)

FOREIGN PATENT DOCUMENTS

EP    2111782 A2    10/2009
JP    2006055324 A    3/2006
(Continued)

OTHER PUBLICATIONS

European Search Report; Application No. EP 12 15 7645; dated Apr. 30, 2012; dated May 8, 2012; 8 pages.

*Primary Examiner* — John P Leubecker
*Assistant Examiner* — Arnaldo Torres Diaz
(74) *Attorney, Agent, or Firm* — Forge IP, PLLC

(57) ABSTRACT

The present invention relates to a steerable catheter device and method of using the same comprising a catheter body having a distal section. The distal section of the catheter body has an inner lumen, and one or more steering lumen radially offset from the inner lumen. The steering lumen comprise a first end having a first diameter and a second end having a second diameter smaller than the first diameter. A fluid source is in fluid communication with the steering lumen for supplying fluid thereto to radially distend the first end of the steering lumen such that the catheter body bends away from the steering lumen. In some cases, a vacuum is supplied to an opposite lumen to further assist bending of the catheter body. The inner lumen may include a porous material that is utilized to clean an instrument, such as an imaging device, movably disposed in the inner lumen.

44 Claims, 7 Drawing Sheets

(51) Int. Cl.
  *A61B 1/015* (2006.01)
  *A61M 25/01* (2006.01)
  *A61M 25/00* (2006.01)
  *A61B 1/00* (2006.01)

(52) U.S. Cl.
  CPC ..... *A61M 25/0013* (2013.01); *A61M 25/0023* (2013.01); *A61M 25/0026* (2013.01); *A61M 25/0052* (2013.01); *A61M 25/0053* (2013.01); *A61M 25/0054* (2013.01); *A61M 2025/0024* (2013.01); *A61M 2025/0059* (2013.01)

(58) Field of Classification Search
  CPC .......... A61M 2025/0059; A61B 1/005; A61B 1/0051; A61B 2017/003
  USPC ...................................................... 600/152
  See application file for complete search history.

(56) References Cited

U.S. PATENT DOCUMENTS

| | | |
|---|---|---|
| 4,890,602 A | 1/1990 | Hake |
| 4,906,230 A | 3/1990 | Maloney et al. |
| 4,909,787 A | 3/1990 | Danforth |
| 4,983,165 A | 1/1991 | Loiterman |
| 5,037,391 A | 8/1991 | Hammerslag et al. |
| 5,054,501 A * | 10/1991 | Chuttani et al. ............ 600/585 |
| 5,308,323 A | 5/1994 | Sogawa et al. |
| 5,313,934 A | 5/1994 | Wiita et al. |
| 5,314,428 A | 5/1994 | Marotta |
| 5,392,766 A | 2/1995 | Masterson et al. |
| 5,415,663 A | 5/1995 | Lazarus et al. |
| 5,619,993 A | 4/1997 | Lee |
| 5,693,015 A * | 12/1997 | Walker et al. ............ 604/96.01 |
| 5,715,817 A * | 2/1998 | Stevens-Wright et al. ... 600/373 |
| 5,860,914 A | 1/1999 | Chiba et al. |
| 5,906,590 A | 5/1999 | Hunjan et al. |
| 5,916,178 A * | 6/1999 | Noone et al. ................. 600/585 |
| 6,083,170 A | 7/2000 | Ben-Haim |
| 6,409,657 B1 | 6/2002 | Kawano |
| 6,527,732 B1 * | 3/2003 | Strauss et al. ................ 600/585 |
| 7,608,056 B2 | 10/2009 | Kennedy, II |
| 7,799,013 B2 * | 9/2010 | Gandras ....................... 604/523 |
| 8,001,984 B2 | 8/2011 | Sasaki |
| 2003/0083613 A1 * | 5/2003 | Schaer ........................ 604/95.04 |
| 2004/0181188 A1 * | 9/2004 | Schaer et al. .............. 604/95.04 |
| 2004/0186378 A1 | 9/2004 | Gesswein |
| 2005/0004433 A1 | 1/2005 | Hirata |
| 2006/0089535 A1 | 4/2006 | Raz et al. |
| 2006/0149129 A1 | 7/2006 | Watts et al. |
| 2007/0060997 A1 | 3/2007 | de Boer |
| 2007/0083082 A1 * | 4/2007 | Kiser et al. .................. 600/115 |
| 2007/0100235 A1 | 5/2007 | Kennedy, II |
| 2008/0147000 A1 * | 6/2008 | Seibel et al. ............... 604/98.01 |
| 2009/0030400 A1 * | 1/2009 | Bose et al. .................... 604/510 |
| 2009/0105543 A1 | 4/2009 | Miller et al. |
| 2009/0250081 A1 | 10/2009 | Gordin et al. |
| 2010/0010437 A1 | 1/2010 | Miles et al. |
| 2010/0168665 A1 * | 7/2010 | Skerven ..................... 604/95.03 |

FOREIGN PATENT DOCUMENTS

| | | |
|---|---|---|
| WO | 9524149 A1 | 9/1995 |
| WO | 2007001217 A1 | 1/2007 |

* cited by examiner

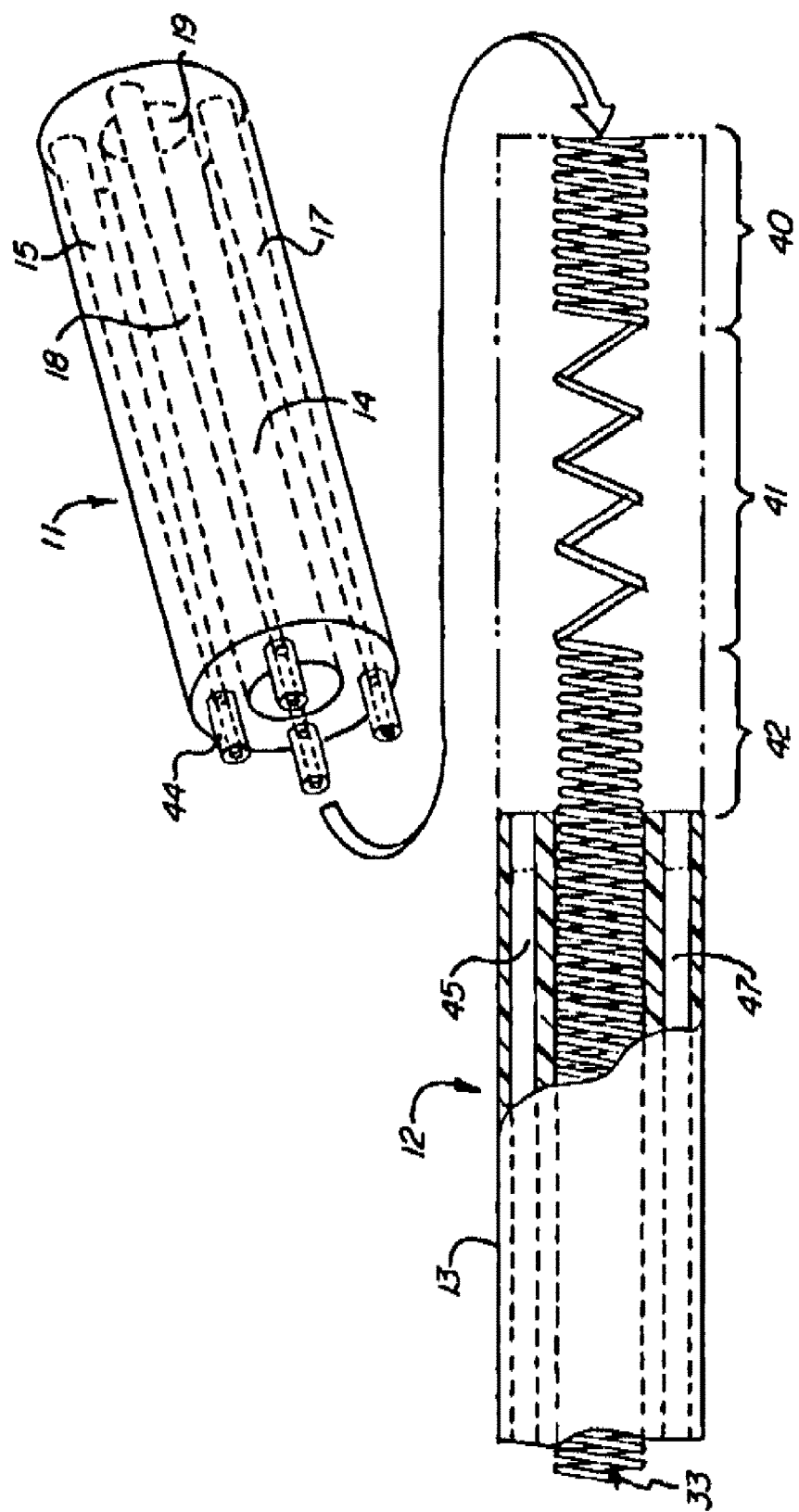

STEERABLE CATHETER

FIELD OF THE INVENTION

The present invention relates to systems and methods for moving a catheter in bodily cavities. More specifically, the present invention relates to a catheter having at least one lumen that expands and/or contracts when at least one of pressure and vacuum is/are applied, which allows the catheter to be steered.

BACKGROUND OF THE INVENTION

In general, catheters are used in medical procedures in which tubular structures, lumens, pleural cavities or spaces of the body, such as airways, vessels, organs and joints, are diagnostically examined and/or therapeutically treated. Catheters, which can be introduced into the body through a natural orifice or through an incision, can deliver imaging devices, surgical instruments, implants, fluids, drugs, pharmacologic materials, biologic materials, biologic agents and therapeutics to treat or remedy various pathologies found therein. Catheters also guide and deliver other components, such as guide wires, scaffolds and tools, to the intended site within the body.

Flexible, semi-rigid and rigid endoscopes are widely used in medicine to provide direct visualization for diagnostic and therapeutic purposes. Flexible, semi-rigid and rigid endoscopes are available in many sizes and configurations intended for use in different parts of the body and for a variety of diagnostic and therapeutic procedures. The visualization device (i.e., a fiber optic image bundle or a sensor at the distal tip of the device), together with the means for illumination, are an integral part of the endoscope. Endoscopes may also provide working channels to guide and deliver other instruments to the desired site. Endoscopes and endoscopic systems are, currently, a reusable and expensive resource in a physician's armamentarium. In addition, the endoscopic equipment systems required to operate endoscopes are often large, bulky and relatively immobile devices.

A limitation in the utility of the flexible endoscope is that their outer diameters are often too large, their inner 'working channel' diameters are often too small, and their lengths are often inadequate to appropriately diagnose and treat the anatomy and corresponding pathologies found in the far reaches of the body's organs, vessels and spaces. A further limitation of the utility of the flexible endoscope is that the articulation of the distal tip, and thus, its maneuverability, is accomplished through two or more wires that run along the body of the flexible endoscope. These wires are attached to complicated mechanical structures that control the wires in manipulating the flexible endoscope's distal tip. As such, the maneuverability is limited by the capabilities of the mechanical structures that control the wire. In addition, optimizing the external and internal diameters of the flexible endoscope is limited by the size and requirements of the wires and their associated mechanical structures.

Additionally, complications sometimes arise when a flexible endoscope malfunctions and it becomes difficult to remove the flexible endoscope from the body.

Many flexible, semi-rigid and rigid endoscopes have openings, or channels, that run through the elongated body of the endoscope. It is through these channels that catheters, in addition to other instruments and devices, are often placed to provide delivery of various therapeutic remedies to treat the anatomy and pathology found therein.

In many cases, catheters are used independent of direct visualization. In these cases, catheters are usually placed in the body using indirect visualization, such as radiography or fluoroscopy. These indirectly visualized catheters are typically used to reach the human heart and the coronary arteries. Here, guide wires, guiding catheters, and catheters with pre-shaped distal tips, some of which are inserted within one another in the effort to reach the desired location within the heart and the coronary arteries, are used. While these devices come in many sizes and lengths, they are made specific to a particular location within the body that is the targeted diagnosis and treatment site. Moreover, in these methods, the articulation of the distal tip is not independent of the body location and the catheter does not have specific controls at the proximal end to sufficiently control or modify the articulation at the distal tip. Consequently, the navigation and maneuverability of catheters requires great skill, relegating their utility and functionality to the experience and competence of the user.

Accordingly, a new class of steerable catheters has been suggested, such as that disclosed in U.S. Pat. No. 7,608,056 to Kennedy, II. Kennedy II discloses a steerable, fluid forced catheter adapted with a tool receiving passageway or working channel, where the distal portion of the catheter body is tapered. The distal end is steered by way of at least one chamber body having a proximal opening and terminating at an occluded distal end, which is offset from the radial central longitudinal axis and positioned within the catheter. The channel body may be operatively coupled to a fluid actuator for injecting and withdrawing fluids to articulate the end portion and steering tip of the catheter through increase and decrease in pressure within the working channel. Radial compression resistant reinforcements (core plug/filler) within the distal end or steerable tip portion inhibit radial inward expansion (ballooning) of the occluded end of a steering channel caused by a change in internal pressure of one or more chamber body occluded ends. Thus, the catheter is steered by axial stretching of the occluded end of channel body(ies) to achieve bending positions ranging from 1 to 15 degrees.

However, this particular device and method suffers from a number of disadvantages and shortcomings. Significantly, the catheter is limited to bending angles of only 1 to 15 degrees, and a vacuum or negative pressure of some type would be required to achieve bending at the higher end of this bending range. Further, the distal steering tip is limited to bending in the axial plane.

U.S. Patent Application Publication No. 2010/0010437 to Miles also discloses a steerable catheter tip with one or more steering lumens each offset from the longitudinal axis of the catheter body. Increasing the internal pressure of one or more of the steering lumens using a pressure source or heating a thermally expansive material in the steering lumen operates to curl the longitudinal axis of the elastomeric cylindrical body. The inner radial wall thickness between each of the steering lumens and the central lumen is greater than the outer radial wall thickness between each of the steering lumens and an outer surface of the tubular sidewall to ensure greater relative expansion along the radially outer region of the sidewall than the radially inner region in order to cause curling towards the direction of the pressurized lumen. As a result, the catheter bends towards the internally pressurized steering lumen(s) for steering the catheter tip, rather than away from the lumen as taught by Kennedy, II.

Thus, it is unclear whether the distal tip of Miles has suitable elasticity and Young's modulus to achieve maximum bend of the distal tip without deformation or fatigue, or whether it has suitable memory to regain and maintain the steerable catheter's elongation and linear rigidity after bending the distal tip and after repetitive bending of the distal tip. It is also unclear if the tip is capable of tight turns of up to 150 degrees.

A further disadvantage of both of the above steerable catheters is that, when an imaging device is employed to help steer the catheter, such as an image fiber or image sensor, there is no mechanism for cleaning the device when it is retracted into the catheter after having been extended out into the bodily cavity.

What is desired, therefore, is a steerable catheter that can be operated using fluid pressure and/or vacuum. What is also desired is steerable catheter that is able to make very tight turns with a short, steerable distal section and where the diameter of the catheter is as small as possible. What is also desired is a steerable catheter with a mechanism for cleaning an imaging device, such as an image fiber or image sensor, that is used to help steer the catheter. What is further desired is to have the above described catheter that can be manufactured at low cost as a disposable product.

SUMMARY OF THE INVENTION

Accordingly, it is an object of the invention to provide a simple to use, lightweight, low cost, highly accurate, steerable catheter system where the catheter can be introduced into the body under direct and/or indirect visualization and can be made portable and disposable.

It is another object of the invention to provide a steerable catheter that serves to eliminate the need to use large wires and complicated mechanical structures to articulate the distal tip of a catheter.

It is a further object of the present invention to provide a steerable catheter having a distal end that is able to bend in as many degrees and planes as possible so that the catheter can be maneuvered through very tight turns within the body, such as airway passages, vessel bifurcations, lumens, pleural cavities, and spaces within the tubular structures and capsular spaces of the body.

It is still another object of the present invention to provide a steerable catheter where the maximum bend of the distal end of the catheter can be achieved with minimum pressures and forces.

It is a further object of the present invention that an imaging device used to help steer the catheter, such as an image fiber or image sensor, may be cleaned as the device is retracted into and extended out of the distal end of the catheter.

In order to overcome the deficiencies of the prior art and to achieve at least some of the objects and advantages listed, the invention comprises a steerable catheter device, including a catheter body having a distal section, the distal section having an inner lumen and a plurality of steering lumens radially offset from the inner lumen, each steering lumen having a first end having a first diameter and a second end having a second diameter smaller than the first diameter, and a fluid source in fluid communication with each of the plurality of steering lumens for supplying at least one of a fluid and a vacuum thereto to change the diameter thereof.

In some embodiments, the distal end of each of the plurality of steering lumens has an end wall, and the end wall moves axially in response to the supply of at least one of a fluid and a vacuum thereto. In certain embodiments, the first end is the distal end of the steering lumen and the second end is the proximal end of the steering lumen. In some cases, each of the plurality of steering lumens has a wall thickness that is smaller at the distal end than at the proximal end.

In certain embodiments, the plurality of steering lumens comprises first, second, third, and fourth steering lumens. In some cases, the fluid source supplies fluid to a first one of the steering lumens while supplying a vacuum to a second one of the steering lumens to bend the catheter body away from the first steering lumen.

In some embodiments, the fluid source is a pump. In some cases, the fluid is a gas.

In certain advantageous embodiments, the system further includes an imaging system movably disposed in the inner lumen. In some embodiments, the distal end of the inner lumen includes porous material, and in some of those cases, the porous material is impregnated with a cleaning solution.

In some embodiments, the distal end of the catheter body comprises silicone. In other embodiments, the invention further includes a coil spring disposed in the inner lumen. In some of those cases, the coil spring has first and second sections, and a middle section between the first and second sections, wherein the coils of the middle section are expanded such that the middle section is more flexible than the first and second sections.

In some embodiments, the catheter body has an outer diameter that is less than about 3 mm. In some of those embodiments, the outer diameter is less than about 2 mm. In certain cases, the inner lumen has a diameter of at least about 1.2 mm.

In some embodiments, each of the plurality of steering lumens includes at least one piezoelectric transducer.

The invention also comprises a steerable catheter device comprising a catheter body having a distal end, the distal end having an inner lumen and a steering lumen radially offset from the inner lumen, the steering lumen having a first end having a first diameter and a second end having a second diameter smaller than the first diameter, and a fluid source in fluid communication with the steering lumen for supplying fluid thereto to radially distend the first end of the steering lumen such that the catheter body bends away from the steering lumen.

In some embodiments, the fluid source further comprises a vacuum source.

The invention also comprises a method of orienting a catheter device within a bodily cavity, the method including positioning a catheter within a bodily cavity, the catheter comprising a catheter body having an inner lumen and a steering lumen radially offset from the inner lumen, the steering lumen having a first end having a first diameter and a second end having a second diameter smaller than the first diameter, and bending the catheter body away from the steering lumen by supplying a fluid to the steering lumen.

In some embodiments, the method further includes the step of bending the catheter body towards the steering lumen by providing a vacuum to the steering lumen. In some cases, the steering lumen is a first steering lumen, the catheter body has a second steering lumen radially offset from the inner lumen, and the step of bending the catheter body away from the first steering lumen further comprises supplying a vacuum to the second steering lumen. In certain embodiments, the steering lumen is a first steering lumen, and the catheter body further includes second, third, and fourth steering lumens.

In some embodiments, the method includes the step of pressing a radially distended portion of a distal end of the catheter body against a bodily cavity wall to provide leverage action to the distal end of the catheter body.

In some embodiments, the step of bending the catheter body away from the steering lumen further includes applying an electrical field across at least one piezoelectric transducer in the steering lumen.

The invention also comprises a method of cleaning an imaging device, the method comprising positioning an imaging device within a lumen of a catheter, the lumen having a distal end including porous material, and moving the imaging device through the porous material.

In some embodiments, the method further includes the step of impregnating the porous material with a cleaning solution.

Other objects of the invention and its particular features and advantages will become more apparent from consideration of the following drawings and accompanying detailed description.

BRIEF DESCRIPTION OF THE DRAWINGS

FIG. 3C is a perspective view of the catheter of FIG. 2 showing a means for disposing spring coil in the inner lumen.

DETAILED DESCRIPTION OF THE INVENTION

Figure 1:
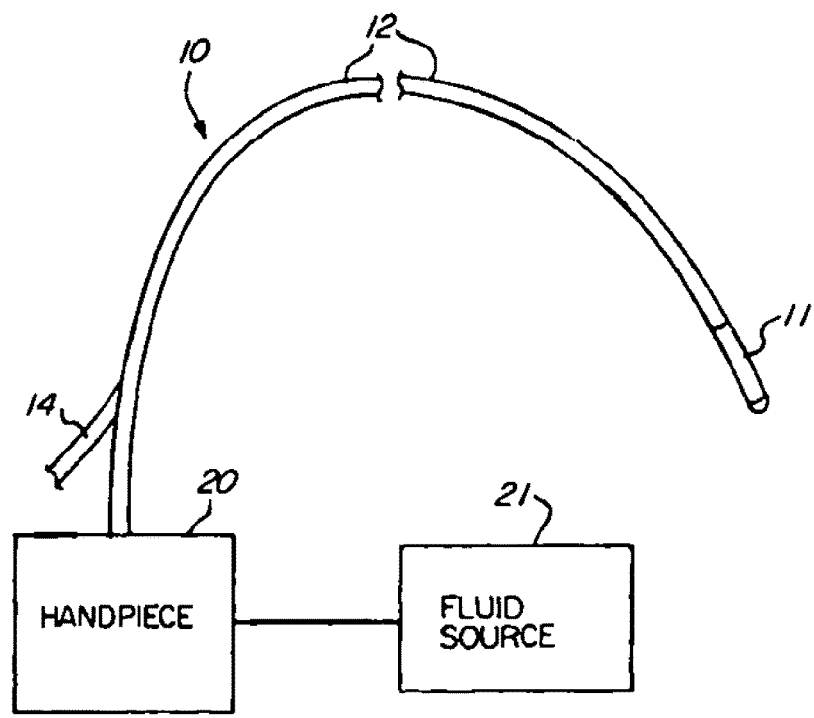
FIG. 1 is a schematic view of a steerable catheter system in accordance with the invention.

The basic components of one embodiment of a steerable catheter in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As shown in FIG. 1, a steerable catheter, generally indicated at reference character (10), includes an elongated catheter body (12) having an elastomeric catheter tip (11) at the distal end, commonly referred to as the distal tip. The catheter (10) is connected to a fluid source (21), which supplies fluid to the catheter body (12), and ultimately, the distal tip (11), via steering lumens disposed therein, as further described below.

The fluid supplied to the steering lumens may be gas or liquid. In certain advantageous embodiments, the fluid is a gas such as pressurized air. In some cases, the fluid source is a pump, such as an electro-pneumatic pump, and includes a vacuum source. The fluid source (21) may be an integral part of the hand piece (20) or visa versa.

Figure 2:
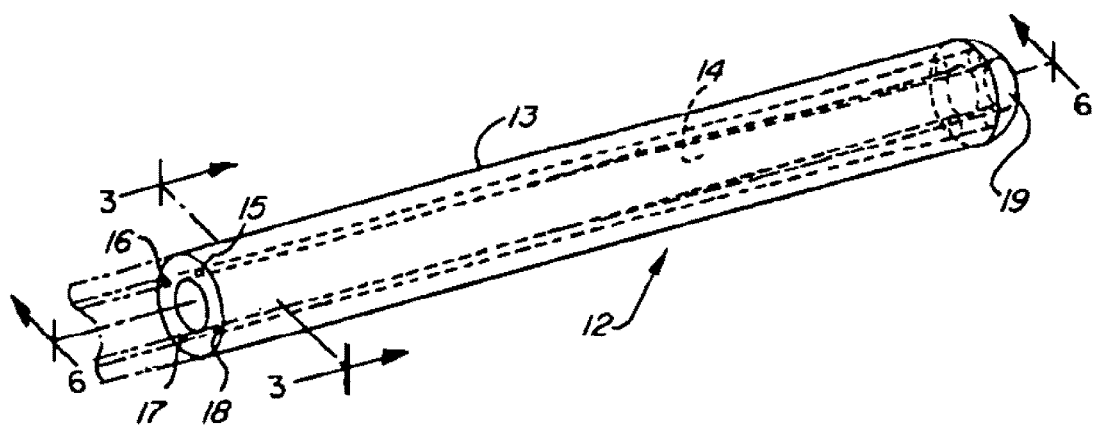
FIG. 2 is a perspective view of the distal end of the catheter of FIG. 1.

As can be seen in FIGS. 1 and 2, the catheter body (12) has a generally cylindrical body that is shown in particular as a tubular member (13) with an inner lumen (14). The cylindrical body (13) has a longitudinal axis (6-6) along which the length of the cylindrical body (13) is defined. Extending through substantially the entire length of the catheter body (12) is at least one, and preferably two or more, steering lumens (15, 16, 17, 18). In particular, as shown in FIGS. 2 and 3, four steering lumens (15, 16, 17, 18) are shown integrally formed in as part of the tubular member (13) surrounding the inner lumen (14). Each steering lumen (15, 16, 17, 18) is shown radially offset from the inner lumen (14) and the longitudinal axis (6-6) of the cylindrical body (12). In certain advantageous embodiments, the inner radial wall thickness of each of the steering lumens (15, 16, 17, 18) is greater at their proximal ends than the inner radial wall thickness of each of the steering lumens (15, 16, 17, 18) at their distal ends.

While various elastomeric materials may be used for the distal tip (11) portion of the catheter body (12), one exemplary material is silicone.

The catheter body (12) is made of a highly elastic material with a low modulus of elasticity with minimized resistance to bending. The elongated catheter body (12) may be constructed using a rigid or semi-rigid material, such as, for example, polyether amide (PEBA). The outer diameter of the catheter should usually be made as small as possible. Typically, the outer diameter is less than about 3 mm. Preferably, the outer diameter of the catheter body is less than 2 mm.

In certain advantageous embodiments, the catheter body (12) includes imaging markers, such as radio opaque rings, located throughout the length of, or at or near, the distal tip (11). Such markers can be selected and appropriately positioned in order to reflect the relevant waves of various imaging modalities (e.g., x-ray) in order to allow the use of such modalities to assist with the precise positioning of the catheter. In another advantageous embodiment, the spring coil is radiopaque.

The inner lumen (14) may be used to deploy various instruments, devices, or fluids into the desired part of the airway, vessel, lumen, or pleural cavity of or other bodily cavity, such as an imaging device, an instrument, a device, or a fluid. The inner lumen (14) may further be divided into a plurality of lumens (not shown), through which an imaging device, an instrument, a device, or a fluid may be placed. The inner lumen(s) can be used to deliver any number of things to assist with opening the cavity, circulation, aspiration, respiration, the decomposition of an obstruction, or the stimulation of healing in the affected area, including air, aspirates, drugs, biologics, biogenetic agents, nano-particulates, solutions, stem cell and gene therapies, and stents and scaffolds. Specifically, the catheter (10) could be used for the deployment of pro-generative vehicles and/or catalysts in the repair, treatment, and therapy of the targeted areas, including biologic, nano-particulate materials and/or biogenetic materials, structures, scaffolds, and similar devices and vehicles, including, for example, bone morphogenetic proteins, microcrystalline nano-particulates, collagens, de-mineralized bone chips, calcium-based structures, poly glycolic acids, poly lactic acids, and hyaluronic acids. The catheter (10) can likewise be used for the deployment of inert, inelastic, and semi-rigid materials, such as, for example, PEEK, ceramic, cobalt chrome, titanium, and stainless steel.

The inner lumen (14) should be as large as possible to easily pass an imaging fiber or an imaging device (as well as an illumination device) having an outer diameter of approximately 1.2 mm, as well as various micro biopsy forceps and drug delivery instruments. Accordingly, in certain advantageous embodiments of the invention, the inner lumen (14) has a diameter of at least about 1.2 mm.

Figure 3A:
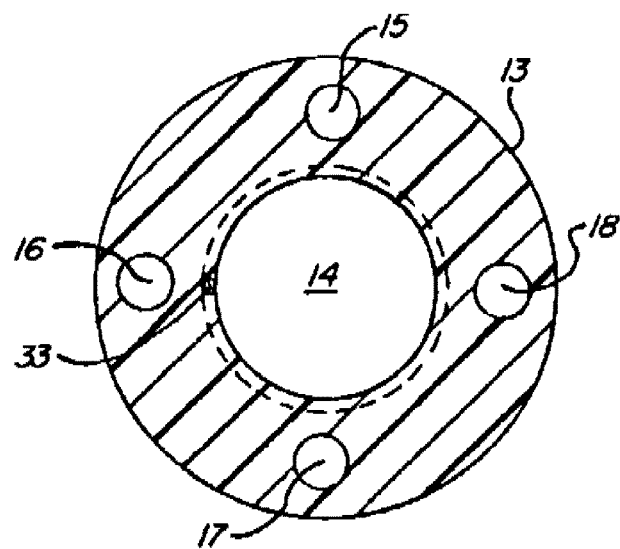
FIG. 3A is a cross-sectional view of the catheter of FIG. 2 along line 3-3.
Figure 3B:
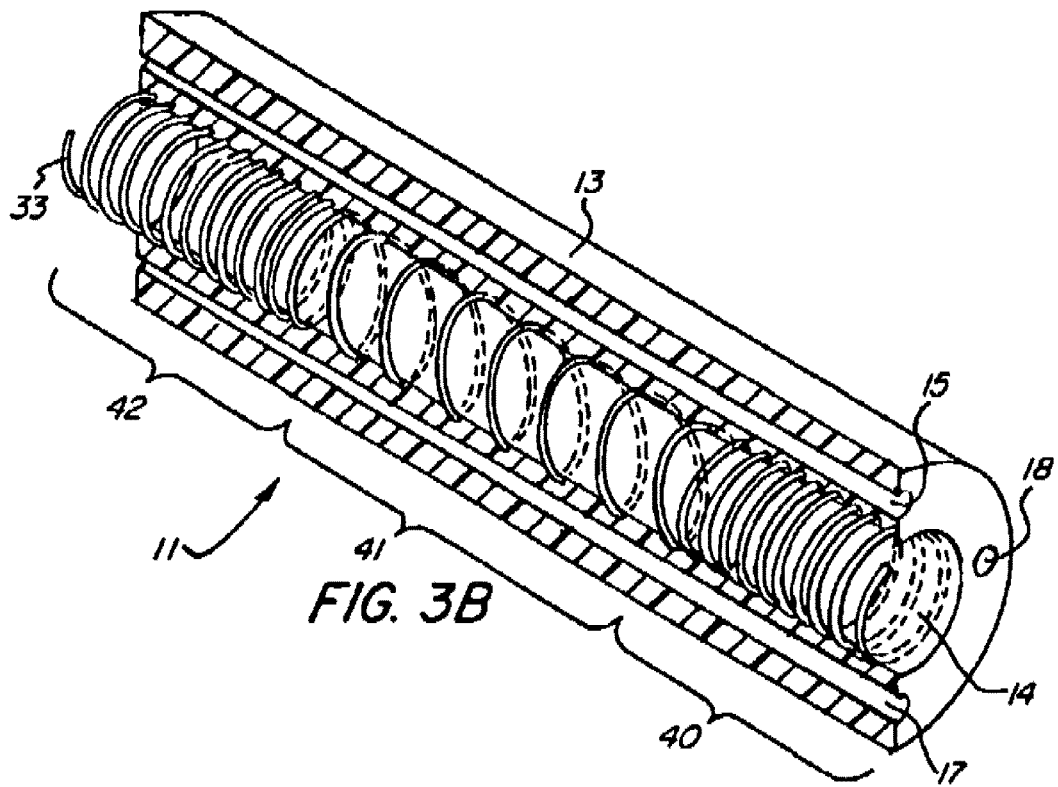
FIG. 3B is a partially cross-sectional view of the catheter of FIG. 2 along the line 6-6

As depicted in FIGS. 3A-3C, the four steering lumens (15, 16, 17, 18) are shown in the four quadrants (i.e., East (18), West (16), North (15) and South (17)) of the inner lumen (14) and spaced approximately equidistant from one another. However, the steering lumens (15, 16, 17, 18) may be spatially separated in any manner that is radially offset from the inner lumen (14). While any one or more of these steering lumens (15, 16, 17, 18) can be filled with pressured air in various amounts, the opposite steering lumen(s) (15, 16, 17, 18) may be deflated with vacuum to facilitate the bending of the distal tip (11).

Although not shown, other lumens can be included along the length of the catheter (10) as auxiliary-working channels to deliver drugs, agents and/or other micro-instruments and/or assist the bending motion of the distal tip.

The inner lumen (14) may be lined with a coil spring (33), depicted by a ring in FIG. 3A, to assist the bending motion of the catheter body and distal tip. The coil spring (33) allows the distal tip to be stiffer and stay straight while the catheter is being pushed through the body vessel. The coil spring (33) can be molded over during the catheter extrusion process and can run the entire length of the catheter. Alternatively, the distal tip (11) and/or catheter body, may be molded or extruded in a first step and the coil spring (33) may be disposed within the inner lumen (14).

FIG. 3B illustrates an advantageous embodiment of the distal tip (11) including a coil spring (33) disposed in the inner lumen (14). The cylindrical body (13) has been extruded around the coil spring (33). In this embodiment, the coils in the center section (41) of the coil spring are expanded to make them more bendable when pressure and or vacuum are applied to the steering lumens (15, 17, 18). The coils at the distal (40) and proximal sections (42) of the coil spring (33) are not expanded, making them more resistant to bending.

FIG. 3C illustrates a method of disposing the inner lumen with coil spring (33). The catheter body (12) and distal tip (11) are provided as separate components. The catheter body (12) comprises the coil spring (33), a portion of which extends outside of the distal portion of the catheter body (12) and remains exposed. The exposed portion of the coil (33) is approximately the same length as the distal tip (11). The catheter body (12) may be extruded around the coil spring (33), or the catheter body (12) may be molded or extruded in a first step and the coil spring (33) may be disposed in the inner lumen as a liner. As shown in FIG. 3C, the exposed portion of the coil spring (33) comprises an expanded center portion (41) surrounded by less expanded coils on the proximal (42) and distal (40) sides of the expanded portion (41). The exposed portion of coil spring (33) may be disposed within the inner lumen (14) of the distal tip (11) by pushing the exposed coil into the inner lumen (14) or sliding the inner lumen (14) over the exposed coil. A locking member (44) comprising a lumen may be provided to facilitate coupling of the distal tip (11) to the catheter body (12). As show in FIG. 3C, the locking member (44) connects the distal portion of steering lumens (15, 17) to a working lumen (45, 47) within the catheter body (12).

As shown in FIG. 2, the steering lumens (15, 16, 17, 18) extend from the proximal end through the elongated catheter body (12) to an endpoint within the elastomeric distal end (11). The diameter of the steering lumens (15, 16, 17, 18) is tapered along the longitudinal axis such that the proximal end has a diameter that is smaller than the diameter at the distal end. This tapering also causes the wall thickness at the distal end to be smaller than the wall thickness at the proximal end. The diameter of the inner lumen (14) is preferably consistent throughout the longitudinal axis. The inner lumen (14) also extends from the proximal end through the elongated catheter body to an opening (19) in the distal end (11). The proximal end of the catheter body (12) provides suitable termination for the steering lumens (15, 16, 17, 18) to be connected to a control hand piece (20), as illustrated in FIG. 1, and the inner lumen (14), or any plurality of inner lumens that may serve as an access port for other instruments, devices or fluids.

Figure 4:
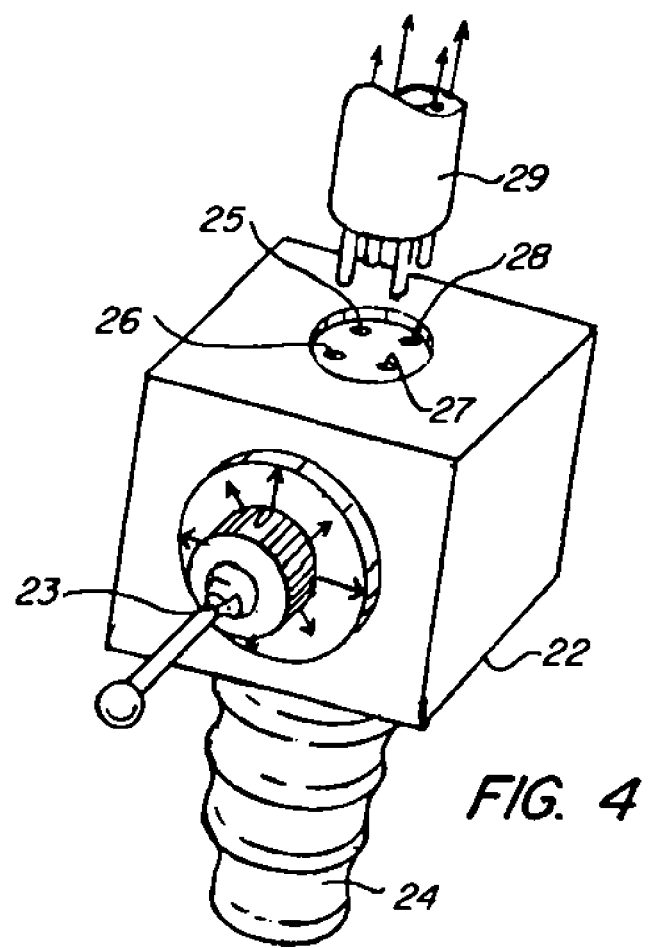
FIG. 4 is an exploded, isometric view of the hand piece of FIG. 1.

As shown in FIGS. 1 and 4, the pressure controller or hand piece (20) is provided for selectively and independently controlling the level of pressurized fluid delivered to each of the steering lumens from the pressurized fluid source. FIG. 4 shows the proximal end (29) of catheter (10) available for connection to a hand held device (22) that includes a control mechanism (23), or a plurality of control mechanisms, that can be articulated to any location along a 360° circle and translated in any plane. In doing so, the distal tip will bend accordingly in three-dimensional space. The device (22) also comprises a connection (24) to a fluid source.

The steering lumens (15, 16, 17, 18) may be coupled to pressure ports (25, 26, 27, 28), which control the flow of fluid from the fluid source to the respective individual steering lumens. The steering lumens (15, 16, 17, 18) may directly couple to the ports (25, 26, 27, 28) for direct control of the pressurized fluid from the pressurized fluid source. Alternatively, another coupling member may be provided for channeling pressurized fluid from the ports (25, 26, 27, 28) to the steering lumens (15, 16, 17, 18). Pressure lines (not shown) may, for example, be molded or extruded into the walls of the elongated catheter body (12) to connect the steering lumens (15, 16, 17, 18) to the pressure ports (25, 26, 27, 28). It is appreciated that the device (22) may include valves and valve control devices/electronics as known in the art.

Microprocessor-controlled solenoid valves may be used to control the fluid flow and vacuum. Additionally, fluid pressure may be continuously monitored by a microcontroller using a pressure regulator at the input from a tank, output of the regulator, and output to the steering lumens (15, 16, 17, 18). Appropriate pressure regulators, such as, for example, Festo model SDET-22T-D10-G14-U-M12, provide to the microcontroller analog electrical signal (0V-10V) inputs that vary proportionally to the pressure at the regulators. The gas may pass through an electronic flow meter, such as a Festo model SFET-F010-L-WQ6-B-K1, and a filter, before being delivered to the steering lumen (15, 16, 17, 18).

Figure 5:
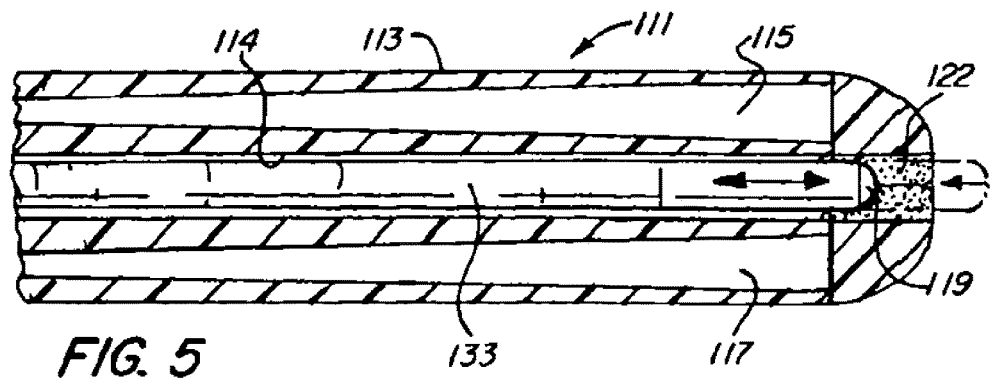
FIG. 5 is a cross-sectional view of the catheter of FIG. 2 along line 6-6 showing an imaging system movable through porous material contained therein.

FIG. 5 illustrates a cross-sectional view along the longitudinal axis of a catheter tip (111). The distal tip (111) comprises an inner lumen (114) and tapered steering lumens (115, 117) having a proximal end diameter that is smaller than diameter at the distal end. This view shows the inner lumen (114) and the steering lumens (115, 117) contained within the tubular member (113) of the distal tip (111). In the illustrated embodiment, the distal opening (119) of the inner lumen (114) is filled with a porous material (122), which allows an instrument (133) or any other device that may be inserted through the inner lumen (114) passage to the bodily cavity. The purpose of this porous material (122), which may be impregnated or soaked with a suitable solution, is to clean any instrument (133) and/or devices as they pass through the porous material (122). In the case of an imaging device, such as an image fiber or image sensor, the lens can be cleaned as the device is retracted into the inner lumen (114) and extended back out of the distal end opening (119).

Figure 6A:
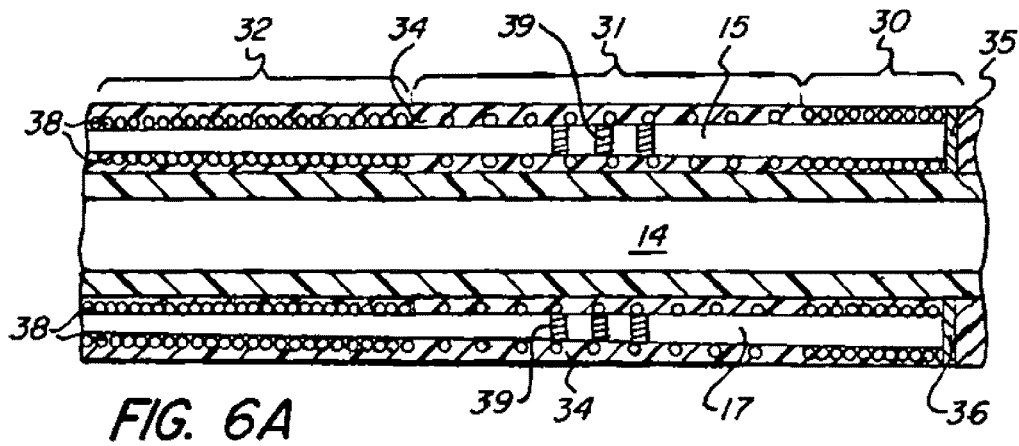
FIG. 6A is a cross-sectional view of an alternative embodiment of the catheter of FIG. 2 along line 6-6.
Figure 6B:
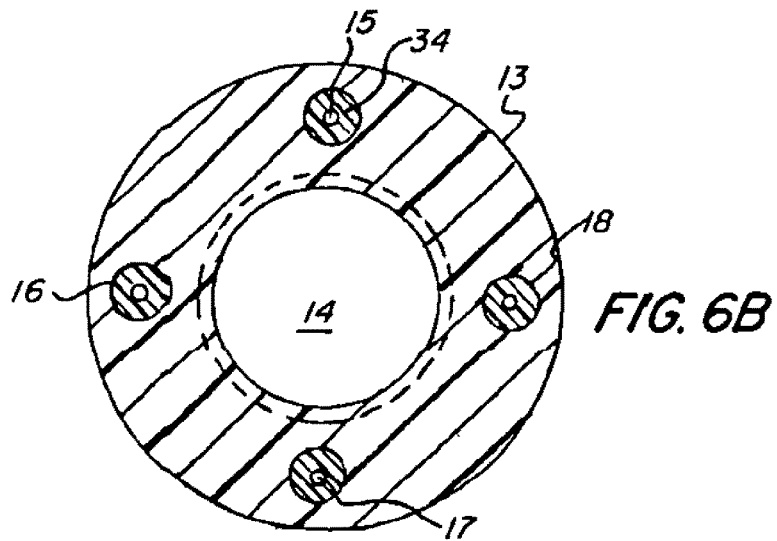
FIG. 6B is a cross-sectional view of the catheter of FIG. 6A.

FIGS. 6A and 6B show an embodiment of the distal tip (11) of a catheter of the present invention in which steering lumens (15, 16, 17, 18) are lined with a silicone liner (34) comprising a coil spring (38). The distal end walls (35, 36) of steering lumens (15, 17) are also shown. As with the inner lumen, the spring coil (38) allows the distal tip to be stiffer and stay straight while the catheter is being pushed through the body vessel. The coils (38) in the center section (31) of the distal tip are expanded to make them more bendable when pressure and or vacuum are applied to the steering lumens. The coils (38) at the distal (30) and proximal sections (32) of the bendable distal tip (11) are not expanded, making them more resistant to bending. The spring coil (38) can be molded over during the catheter extrusion process and can run the entire length of the catheter or can be disposed within the steering lumen after extrusion. The liner (34) can also include electrical conductors to power micro-device components, such as piezoelectric devices (39) and/or sensors, such as pressure and temperature transducers.

Figure 7A:
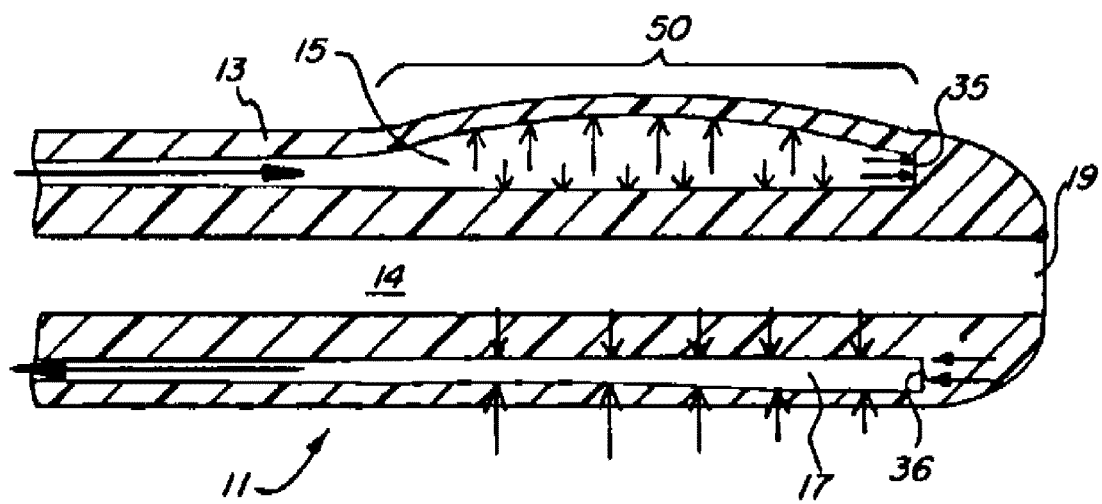
FIG. 7A is a cross-sectional view of the catheter of FIG. 2 along line 6-6 as pressure and vacuum are applied to the steering lumens.
Figure 7B:
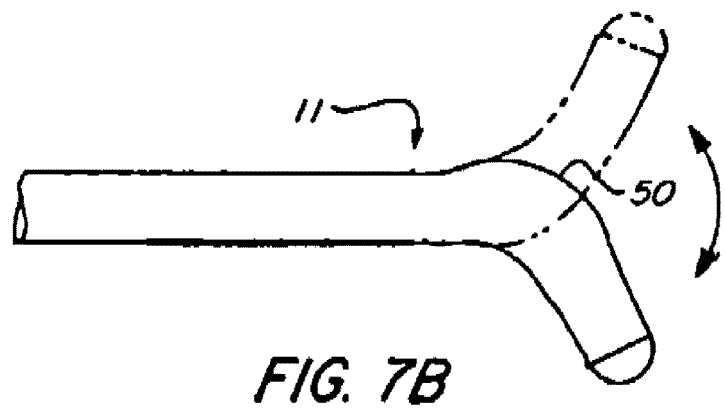
FIG. 7B is a perspective view of the steerable catheter of FIG. 7A with pressure and vacuum applied to the steering lumens.

FIGS. 7A and 7B illustrate distending forces caused by applying fluid from a fluid source (21), such as the below described pump, to the elastomeric distal end (11) of the catheter of FIG. 2, 3A-C or 6A-B. FIG. 7A is a cross-sectional view showing the direction of internal fluid pressure in steering lumen (15) as pressure is increased and the direction of internal pressure in steering lumen (17) as vacuum is applied. FIG. 7B is a perspective view of the bending of elastomeric catheter tip (11) of FIG. 7A that is achieved after the internal pressure in steering lumen (15) is increased and vacuum is simultaneously applied to steering lumen (17).

When positive pressure is supplied to steering lumen (15), radial forces which expand the cylindrical body (13) are produced. Additionally, force is supplied to the lumen end wall (35), axially expanding the lumen (15) and the distal tip (11). The radial forces acting on the cylindrical body (13) in combination with any expanded coil in the center section of the distal tip (11) and the increased diameter of the steering lumen (15) at its distal end cause greater radial expansion (ballooning effect), which radially distends the adjacent portion (50) of the catheter distal tip (11). When negative pressure or vacuum is applied to steering lumen (17), the vacuum provides radial and axial forces opposite those produced by the application of positive pressure, contracting the lumen sidewall and end wall (36) and, in turn, the adjacent wall of the distal tip (11).

It is advantageous that as the lumen (15) is pressurized, the corresponding lumen in the opposite quadrant (17) is provided a vacuum. This creates bending with a smaller radius (less than 0.5 inch). It is notable that bending of the distal end (11) is not a jointed bending/hinging of segments at various joint/hinge points. Rather, it produces a bent curve along the length of the distal end (11). As previously discussed, the steering lumens (15, 17) are tapered such that the inner diameter is greater at the distal end than at the proximal end, and the inner radial wall thickness is smaller at the distal end than at the proximal end. This is so that, when the steering lumen is pressurized and distended, such as in FIGS. 7A and 7B, there is greater relative expansion in the flexible distal end than in the elongated catheter body. The application of vacuum allows the ballooning effect to have an even greater contribution than with positive pressure alone.

A pump that may be used to provide the fluid source described above will hereafter be described. The pump may include an air compressor and a pressure tank, such as a Festo model CRVZS-0.1. The air pressure in the tank may be continuously monitored by a microcontroller which initiates the compressor to operate via an electrical signal output when the tank pressure drops below a certain pressure and displays the amount of air in the tank. A check valve, such as a Festo model H-1/8-A/1, may be located between the compressor and the tank in order to prevent the pressured gas from flowing back into the compressor. In another variation of the pump, the above-referenced compressor and pressure tank are not included, and the pressurized air or carbon dioxide is instead provided from an external source, such as gas tank or the operating room walls commonly found in an operating room.

In certain advantageous embodiments, a vacuum source, such as a Festo model VN-05-L-T3-PQ2-VQ2-R01-B, may also be included in the pump so that negative pressure can be applied to the steering lumen (15, 16, 17, 18). The vacuum source may be turned on and off by a microcontroller via an electrical output signal.

In certain embodiments, a front panel of the pump includes an interface for the hand piece (20), as previously described. This hand piece (20) can be hardwired or wirelessly connected to the pump using readily available communication technologies, such as infrared or radio frequency (e.g., Bluetooth).

The invention is also meant to encompass steerable catheters having only a single steering lumen. Such a single steering lumen embodiment could be rotated about its longitudinal axis in order to change the bending direction of the elastomeric catheter tip.

One method of orienting a catheter device within a bodily cavity involves positioning any of the catheters described herein within a bodily cavity and supplying a fluid to at least one steering lumen, preferably with a pump of the type described above. One can then control the fluid supply within the distal end of the steering lumen via a hand piece, as described above. In certain advantageous embodiments, one would position a catheter comprising a plurality of steering lumens within the bodily cavity and provide vacuum to at least one steering lumen while another lumen is simultaneously supplied with positive pressure. The above methods enable a catheter to achieve very tight turns up to 150° with a short steerable distal section.

Figure 8:
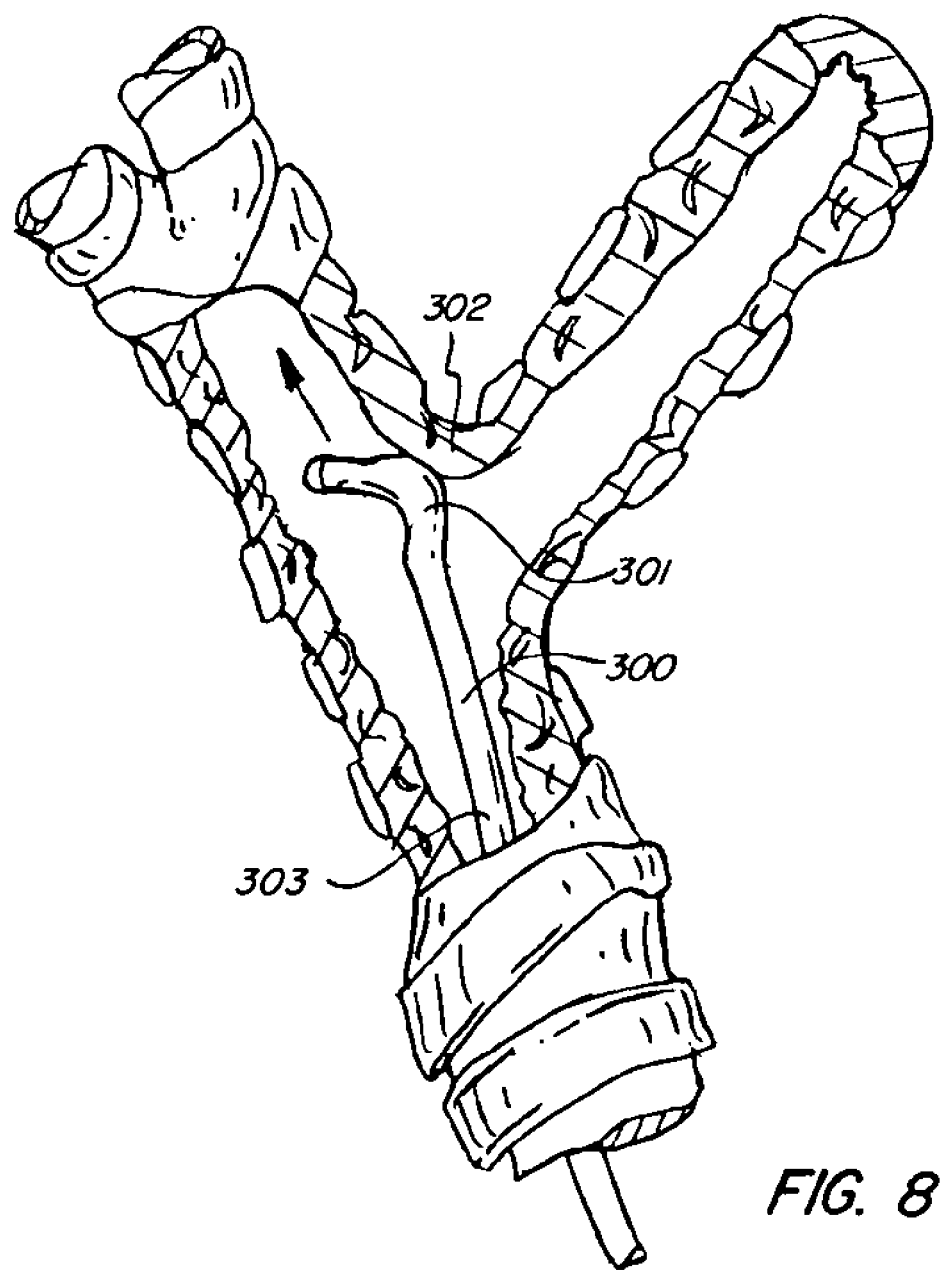
FIG. 8 is a partially exposed, perspective view of the catheter of FIG. 2 being used in a bodily cavity.

Another method of orienting a catheter device (300) within a bodily cavity is illustrated in FIG. 8. The method involves positioning a catheter (300) including a catheter body (303) having a distal end, the distal end comprising at least one inner lumen (not shown) and a steering lumen (not shown) radially offset from the inner lumen within a bodily cavity and supplying a fluid to at least one of the steering lumen(s). As described above, the steering lumen has a distal end having a first diameter and a proximal end having a second diameter smaller than the second diameter. Upon fluid supply to the at least one steering lumen, the resultant radially distended portion of the catheter body (301) is pressed against a bodily cavity wall (302) to provide leverage action to the distal end of the catheter body. The leverage action further bends the tip of the catheter in the desired direction and enables tighter turns than are possible by supply of fluid to the steering lumen(s) alone.

Another method of bending the distal end of the catheter is achieved by incorporating piezoelectric transducers in the catheter body, as shown in FIG. 6B. Piezoelectric transducers may be stacked along the longitudinal axis of the catheter body with spacing material in-between them. Application of an electrical field across each of the transducers causes them to expand or contract, which generates strong longitudinal forces that stretch or squeeze the flexible second end portion material and bends the flexible second end portion in a desired direction.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A steerable catheter device comprising:
a catheter body having a distal section, the distal section having
an inner lumen; and
a plurality of steering lumens radially offset from said inner lumen, each steering lumen having a first end having a first diameter and a second end having a second diameter smaller than the first diameter; and
a fluid source in fluid communication with each of said plurality of steering lumens for supplying at least one of a fluid and a vacuum thereto to change the first diameter thereof.

2. The catheter of claim 1, wherein:
the distal end of each of said plurality of steering lumens has an end wall; and
said end wall moves axially in response to the supply of at least one of a fluid and a vacuum thereto.

3. The catheter of claim 2, wherein each of said plurality of steering lumens has a wall thickness that is smaller at the distal end than at the proximal end.

4. The catheter of claim 1, wherein the first end is the distal end of the steering lumen and the second end is the proximal end of the steering lumen.

5. The catheter of claim 1, wherein the plurality of steering lumens comprises first, second, third, and fourth steering lumens.

6. The catheter of claim 1, wherein said fluid source supplies fluid to a first one of said steering lumens while supplying a vacuum to a second one of said steering lumens to bend said catheter body away from the first steering lumen.

7. The catheter of claim 1, wherein the fluid source is a pump.

8. The catheter of claim 1, wherein the fluid is a gas.

9. The catheter of claim 1, further comprising an imaging system movably disposed in said inner lumen.

10. The catheter of claim 1, wherein the distal end of said inner lumen includes porous material.

11. The catheter of claim 10, wherein the porous material is impregnated with a cleaning solution.

12. The catheter of claim 11, further comprising an imaging system movably disposed in said inner lumen and through said porous material.

13. The catheter of claim 1, wherein the distal section of said catheter body comprises silicone.

14. The catheter of claim 1, further comprising a coil spring disposed in said inner lumen.

15. The catheter of claim 14, wherein said coil spring has first and second sections, and a middle section between the first and second sections, wherein the coils of the middle section are expanded such that the middle section is more flexible than the first and second sections.

16. The catheter of claim 1, wherein each of said plurality of steering lumens includes at least one piezoelectrical transducer therein.

17. The catheter of claim 1, wherein said catheter body has an outer diameter that is less than about 3 mm.

18. The catheter of claim 17, wherein said outer diameter is less than about 2 mm.

19. The catheter of claim 1, wherein said inner lumen has a diameter of at least about 1.2 mm.

20. A steerable catheter device comprising:
a catheter body having a distal section, the distal section having
an inner lumen; and
a steering lumen radially offset from said inner lumen, said steering lumen having a first end having a first diameter and a second end having a second diameter smaller than the first diameter; and
a fluid source in fluid communication with said steering lumen for supplying fluid thereto to radially distend the first end of said steering lumen such that said catheter body bends away from said steering lumen.

21. The catheter of claim 20, wherein:
the distal end of said steering lumen has an end wall; and
said end wall moves axially in response to the supply of fluid to said steering lumen.

22. The catheter of claim 20, wherein the first end is the distal end of the steering lumen and the second end is the proximal end of the steering lumen.

23. The catheter of claim 20, wherein said steering lumen has a wall thickness that is smaller at the distal end than at the proximal end of said steering lumen.

24. The catheter of claim 20, wherein the fluid source further comprises a vacuum source.

25. The catheter of claim 20, wherein the fluid source is a pump.

26. The catheter of claim 20, wherein the fluid is a gas.

27. The catheter of claim 20, further comprising an imaging system movably disposed in said inner lumen.

28. The catheter of claim 20, wherein said inner lumen has a distal end that includes porous material.

29. The catheter of claim 28, wherein the porous material is impregnated with a cleaning solution.

30. The catheter of claim 29, further comprising an imaging system movably disposed in said inner lumen and through said porous material.

31. The catheter of claim 20, wherein the distal section of said catheter body comprises silicone.

32. The catheter of claim 20, further comprising a coil spring disposed in said inner lumen.

33. The catheter of claim 32, wherein said coil spring has first and second sections, and a middle section between the first and second sections, wherein the coils of the middle section are expanded such that the middle section is more flexible than the first and second sections.

34. The catheter of claim 20, wherein said catheter includes an imaging marker.

35. The catheter of claim 20, wherein said steering lumen includes at least one piezoelectrical transducer therein.

36. A method of orienting a catheter device within a bodily cavity, the method comprising:
   positioning a catheter within a bodily cavity, the catheter comprising a catheter body having an inner lumen and a steering lumen radially offset from the inner lumen, the steering lumen having a first end having a first diameter and a second end having a second diameter smaller than the first diameter; and
   bending the catheter body away from the steering lumen by supplying a fluid to radially distend the steering lumen.

37. The method of claim 36, further comprising the step of bending the catheter body towards the steering lumen by providing a vacuum to the steering lumen.

38. The method of claim 36, wherein the steering lumen is a first steering lumen, the catheter body has a second steering lumen radially offset from the inner lumen, and the step of bending the catheter body away from the first steering lumen further comprises supplying a vacuum to the second steering lumen.

39. The method of claim 36, wherein the steering lumen is a first steering lumen, and the catheter body further includes second, third, and fourth steering lumens.

40. The method of claim 36, further comprising the step of pressing a radially distended portion of a distal end of the catheter body against a bodily cavity wall to provide leverage action to the distal end of the catheter body.

41. The catheter of claim 36, wherein the first end is the distal end of the steering lumen and the second end is the proximal end of the steering lumen.

42. The catheter of claim 36, wherein the steering lumen includes at least one piezoelectric transducer therein, wherein the step of bending the catheter body away from the steering lumen further comprises applying an electrical field across the at least one piezoelectric transducer.

43. A method of cleaning an imaging device, the method comprising:
   positioning an imaging device within the inner lumen of the catheter of claim 1, the inner lumen having a distal end including porous material; and
   moving the imaging device through the porous material.

44. The method of claim 43, further comprising the step of impregnating the porous material with a cleaning solution.

* * * * *